US012220394B2

(12) United States Patent
Wada et al.

(10) Patent No.: US 12,220,394 B2
(45) Date of Patent: Feb. 11, 2025

(54) PHARMACEUTICAL COMPOSITION FOR PREVENTION OR TREATMENT OF KIDNEY DAMAGE

(71) Applicants: National University Corporation Kanazawa University, Kanazawa (JP); Kagami Inc., Ibaraki (JP)

(72) Inventors: Takashi Wada, Ishikawa (JP); Kengo Furuichi, Ishikawa (JP); Norihiko Sakai, Ishikawa (JP); Yasunori Iwata, Ishikawa (JP); Akinori Hara, Ishikawa (JP); Yusuke Nakade, Ishikawa (JP); Kenji Hamase, Fukuoka (JP); Masashi Mita, Tokyo (JP)

(73) Assignees: National University Corporation Kanazawa University, Kanazawa (JP); Kagami Inc., Ibaraki (JP)

( * ) Notice: Subject to any disclaimer, the term of this patent is extended or adjusted under 35 U.S.C. 154(b) by 1040 days.

(21) Appl. No.: 16/972,898

(22) PCT Filed: Jun. 6, 2019

(86) PCT No.: PCT/JP2019/022607
§ 371 (c)(1),
(2) Date: Dec. 7, 2020

(87) PCT Pub. No.: WO2019/235559
PCT Pub. Date: Dec. 12, 2019

(65) Prior Publication Data
US 2021/0220309 A1 Jul. 22, 2021

(30) Foreign Application Priority Data
Jun. 7, 2018 (JP) ................. 2018-109731

(51) Int. Cl.
*A61K 31/198* (2006.01)
*A61K 9/00* (2006.01)
*A61P 13/12* (2006.01)

(52) U.S. Cl.
CPC .......... *A61K 31/198* (2013.01); *A61K 9/0053* (2013.01); *A61P 13/12* (2018.01)

(58) Field of Classification Search
CPC ...... A61K 31/198; A61K 9/0053; A61P 13/12
See application file for complete search history.

(56) References Cited

U.S. PATENT DOCUMENTS

| 2015/0079623 A1 | 3/2015 | Hamase et al. |
| 2015/0141514 A1 | 5/2015 | Morita et al. |
| 2015/0352067 A1 | 12/2015 | Morita et al. |
| 2020/0281962 A1 | 9/2020 | Rink et al. |

FOREIGN PATENT DOCUMENTS

| JP | 2012-502026 A | 1/2012 |
| WO | WO-2010/027344 A1 | 3/2010 |
| WO | WO-2013/140785 A1 | 9/2013 |
| WO | WO-2014/003154 A1 | 1/2014 |
| WO | WO-2014/112641 A1 | 7/2014 |
| WO | WO-2017/106690 A1 | 6/2017 |

OTHER PUBLICATIONS

Kaltenbach et al., "Compounds Protective against Renal Tubular Necrosis Induced by D-Serine and D-2,3-Diaminopropionic Acid in the Rat," Experimental and Molecular Pathology, 1983, 37:225-234. (Year: 1983).*
Kaltenbach et al., "Compounds Protective against Renal Tubular Necrosis Induced by D-Serine and D-2,3-Diaminopropionic Acid in the Rat," Experimental and Molecular Pathology, 1983, 37:225-234.
KDIGO 2012 Clinical Practice Guideline for the Evaluation and Management of Chronic Kidney Disease, Kidney International Supplements 1, 2013, 163 pages.
Takayama et al., "A simple method for producing a model of kidney dysfunction in rats and mice—Acute and chronic kidney disease models-", Folia Pharmacol. Jpn., 2008, 131:37-42, with English translation.
Sasabe et al., "Ischemic Acute Kidney Injury Perturbs Homeostasis of Serine Enantiomers in the Body Fluid in Mice: Early Detection of Renal Dysfunction Using the Ratio of Serine Enantiomers," Plos One, Jan. 29, 2014, 9(1):e86504, 1-9.

* cited by examiner

*Primary Examiner* — Samantha L Shterengarts
*Assistant Examiner* — Jed A Kucharczk
(74) *Attorney, Agent, or Firm* — Foley & Lardner LLP (57) ABSTRACT

The present invention pertains to a pharmaceutical composition for the prevention or treatment of kidney disease, a kidney inflammation inhibitor, an inflammatory cell death inhibitor for the kidneys, or a food for the prevention or improvement of kidney disease, that include D-alanine or a derivative thereof. In addition, the present invention pertains to the use of D-alanine or a derivative thereof, for the production of a pharmaceutical composition for the prevention or treatment of kidney disease.

6 Claims, 5 Drawing Sheets
Specification includes a Sequence Listing.

```
SEQUENCE LISTING

<160> NUMBER OF SEQ ID NOS: 2

<210> SEQ ID NO 1
<211> LENGTH: 20
<212> TYPE: DNA
<213> ORGANISM: Artificial Sequence
<220> FEATURE:
<223> OTHER INFORMATION: KIM-1 Forward Primer

<400> SEQUENCE: 1
aggaagaccc acggctattt                                           20

<210> SEQ ID NO 2
<211> LENGTH: 20
<212> TYPE: DNA
<213> ORGANISM: Artificial Sequence
<220> FEATURE:
<223> OTHER INFORMATION: KIM-1 Reverse Primer
```

```
<400> SEQUENCE: 2
tgtcacagtg ccattccagt                                              20
```

PHARMACEUTICAL COMPOSITION FOR PREVENTION OR TREATMENT OF KIDNEY DAMAGE

CROSS-REFERENCE TO RELATED APPLICATIONS

This application is the U.S. National Stage of PCT/JP2019/022607, filed Jun. 6, 2019, which claims priority to JP 2018-109731, filed Jun. 7, 2018.

FIELD

The present invention relates to a pharmaceutical composition for prevention or treatment of kidney disorder, and specifically it relates to a suppressor of kidney inflammation, to an inflammatory cell death inhibitor, to foods for prevention or treatment of kidney disorder, and to a kidney protective agent.

BACKGROUND

The kidneys are organs that filter waste products and excess water in blood and excrete them as urine, and in addition to maintaining body fluid homeostasis, they also perform a role in blood pressure, hematopoiesis and bone metabolism by endocrine functions. The kidneys can be damaged and undergo reduced function by causes such as immune system disorders, drugs, hypertension, diabetes, hemorrhage or acute drop in blood pressure, infection, or dehydration accompanying burn. Such conditions are referred to as kidney disease, with diabetic kidney disease being one that is caused by diabetes.

Acute kidney injury (AKI) is a kidney disorder that has a course of several hours to several weeks until onset. Acute kidney injury is a state of sudden reduction in renal function caused by ischemia, drugs or endotoxic shock, which produces increased blood concentrations of urea nitrogen or creatinine as body metabolites and symptoms such as abnormal electrolyte metabolism or acidosis, and it is generally diagnosed by a drastic increase in blood creatinine.

Chronic kidney disease (CKD) is a condition attributed to a variety of different kidney disorders, producing either reduced renal function indicated by glomerular filtration rate, or chronic findings (three months or longer) suggesting persistent kidney disorder. Chronic kidney disease affects 13.3 million people in Japan, representing about 13% of the adult population, and as it increases the risk of end-stage kidney disease (ESKD), it poses a threat to national health. No effective method of treatment exists for chronic kidney disease, and as the disease progresses, it leads to reduced renal function and symptoms of uremia, finally requiring renal replacement therapy such as dialysis or kidney transplant, thereby creating a huge burden on the health system and the economy (NPL 1). Because chronic kidney disease exhibits no subjective symptoms until renal function is notably reduced, it is desirable to develop useful biomarkers for early detection and inhibited progression.

Biomarkers for kidney disease include creatinine and urea nitrogen (BUN) which are waste products excreted in urine, as well as NGAL expressed by inflammatory cells, and KIM-1 expressed by damaged proximal tubular epithelial cells, but such markers have been less than satisfactory as early biomarkers. In recent years it has become possible to measure D-amino acids in blood and urine, indicating a potential for D-amino acids as a kidney disease biomarker (PTL 1).

With kidney disease, changes in D-amino acid levels in blood and urine have been reported as being affected by enterobacteria metabolism. In recent metabolomics research, it has been shown that short chain fatty acids derived from enterobacteria affect proliferation of regulatory T cells, and that metabolites play an important role in maintenance of homeostasis and protection of organs. However, there has been no mention of the effects of intestinal bacterial flora-derived D-amino acids on disorders or protection of the organs.

CITATION LIST

Patent Literature

[PTL 1] International Patent Publication No. WO2013/140785

Non Patent Literature

[NPL 1] KDIGO 2012 Clinical Practice Guideline for the Evaluation and Management of Chronic Kidney Disease, Kidney International Supplements 1 (2013)

SUMMARY

Technical Problem

It is desirable to develop drugs that treat or prevent kidney disease or have protective effects on the kidneys.

Solution to Problem

As a result of avid research on D-alanine which corresponds to disease-related changes in the bodies of kidney disease patients, and on its physiological action, the present inventors have found that D-alanine has a protective effect on the kidneys and has a therapeutic and prophylactic effect against kidney disease, and the present invention has been completed based on this finding.

Specifically, the present invention relates to the following inventions:

[1] A pharmaceutical composition for prevention or treatment of kidney disease, comprising D-alanine or its derivative.

[2] The pharmaceutical composition according to [1] above, wherein the pharmaceutical composition for prevention or treatment is used for kidney protection or restoration of renal function.

[3] The pharmaceutical composition according to [1] or [2], wherein the kidney disease includes acute kidney injury and chronic kidney disease.

[4] The pharmaceutical composition according to [1] or [2], wherein the kidney disease is ischemic kidney disorder.

[5] The pharmaceutical composition according to any one of [1] to [4] above, which is to be used in local administration, enteral administration or parenteral administration.

[6] The pharmaceutical composition according to any one of [1] to [5] above, wherein the derivative is a compound that is converted to D-alanine after being administered.

[7] A suppressor of kidney inflammation, comprising D-alanine or its derivative.

[8] A kidney inflammatory cell death inhibitor, comprising D-alanine or its derivative.

[9] A prophylactic or ameliorative food for kidney disease, comprising D-alanine or its derivative.

[10] The prophylactic or ameliorative food for kidney disease according to [9] above, wherein the derivative is a compound that is converted to D-alanine after being administered.

[11] A method for prevention or treatment of kidney disease, which includes administering D-alanine or its derivative.

[12] D-alanine or its derivative, for use in prevention or treatment of kidney disease.

[13] The use of D-alanine or its derivative for production of a pharmaceutical composition for prevention or treatment of kidney disease.

[14] The method, D-alanine or its derivative, or use according to any one of [11] to [13] above, which is to be used for kidney protection or for restoration of renal function.

[15] The method, D-alanine or its derivative or use according to any one of [11] to [14] above, wherein the kidney disease includes acute kidney injury and chronic kidney disease.

[16] The method, D-alanine or its derivative or use according to any one of [11] to [15] above, wherein the kidney disease is ischemia-induced or inflammation-induced kidney disorder.

[17] The method, D-alanine or its derivative or use according to any one of [11] to [16] above, which is to be used in local administration, enteral administration or parenteral administration.

[18] The method, D-alanine or its derivative or use according to any one of [11] to [17] above, wherein the derivative is a compound that is converted to D-alanine after being administered.

Advantageous Effects of Invention

D-Alanine in blood exhibits at least one function or effect from among therapeutic effects on kidney disease such as a kidney protecting effect, anti-inflammatory effect and inflammatory cell death inhibiting effect, and renal function restoration effects.

DESCRIPTION OF EMBODIMENTS

One aspect of the invention relates to a pharmaceutical composition for prevention or treatment of kidney disorder comprising D-alanine or its derivative.

D-Alanine is an optical isomer of L-alanine, one of the constituent amino acids of proteins. According to the invention, the D-alanine may be in the form of any salt such as an acidic salt, basic salt or amphoteric salt, so long as it is a physiologically acceptable salt, such as a hydrochloride, sulfuric acid salt, nitric acid salt, sodium salt, potassium salt, calcium salt or ammonium salt.

A D-alanine derivative is a compound that causes a change in hydrophobic or electrostatic property, or which allows the D-alanine concentration in blood or tissues to be increased after being administered. Any D-alanine derivative may be used that allows the concentration of D-alanine in blood or tissues to be adjusted to the optimal level. Examples of D-alanine derivatives include compounds wherein the carboxy or amino group of D-alanine is protected or substituted. The carboxy group may be esterified or amidated. The amino group may be amidated. Examples of derivatives include D-alanine methyl ester and D-alanine ethyl ester, and peptides including D-alanine, such as dipeptides, tripeptides, oligopeptides or polypeptides.

When a peptide is used, it may consist of alanine alone, or it may comprise other amino acids such as serine, glycine, valine, leucine, isoleucine, threonine, cysteine, methionine, aspartic acid, glutamic acid, asparagine, glutamine, lysine, arginine, phenylalanine, tyrosine, tryptophan or histidine in addition to alanine. Amino acids other than D-alanine may be in either the L-form or D-form. A D-alanine residue, or D-alanine produced by decomposition, may also have a physiological effect, such as a kidney-protecting effect.

Kidney disease is determined based on proteinuria or glomerular filtration rate (GFR). Chronic kidney disease is diagnosed as such if either or both of the following, i.e.

(1) Clear presence of kidney disorder based on urinalysis, image diagnosis, blood examination or pathology, and particularly proteinuria of 0.15 g/gCr or greater (albuminuria of 30 mg/gCr or greater), and (2) Glomerular filtration rate of less than 60 mL/min/1.73 $m^2$, continues for 3 months or longer. The glomerular filtration rate can be determined by calculating the estimated glomerular filtration rate from serum creatinine value, age and gender.

Chronic kidney disease can be caused by a variety of different factors. Risk of kidney disease is associated with diabetes, hypertension, nephritis, polycystic kidney, kidney transplant, dyslipidemia or obesity. According to the invention, therefore, D-alanine or its derivative can be administered to a subject having these kidney disease risks. The target of treatment may also be a subject for whom reduced renal function has been assessed based on health examination. An example of health examination is examination of renal function based on urine protein, urine fresh blood, BUN, creatinine or eGFR, and subjects found to have mild abnormality or subjects requiring follow-up in one or more of these examinations may be considered to have risk of kidney disease. The D-alanine or its derivative may also be administered to a patient suffering from kidney disease in the hope of restoring or preventing deterioration of renal function.

KIM-1 (Kidney injury molecule-1), used as a biomarker for kidney disease, is a single transmembrane protein with a total length of 104 kDa, whose expression is induced in proximal tubular epithelial cells during repair and regeneration following damage. KIM-1 functions as a receptor for the eat-me signal expressed on the surfaces of cells that have undergone apoptosis, and it is thought that KIM-1 contributes to removal of dead cells.

Acute kidney injury is a disease in which renal function is rapidly reduced during a period of several hours to several days, and it can be mainly classified as ischemic injury or injury due to nephrotoxic substances. When the kidney is not supplied with sufficient blood as a result of shock by hemorrhaging or the like, inflammation occurs in the renal tubules or nephrons of the kidney, leading to loss of function. Nephrotoxic substances include agricultural chemicals, drugs, contrast agents and antibiotics, with renal function being lost due to damage to nephrons by such substances. The kidney disease may be classified as prerenal, renal or postrenal, depending on the site of damage. Prerenal kidney disease, being a systemic disease, is caused by reduced blood flow to the kidneys, and its causes include dehydration, shock, burn, massive hemorrhage, congestive heart failure, hepatic cirrhosis or renal artery stenosis. Renal kidney disease arises from the kidneys themselves, and its causes include blood flow disturbance in the kidneys, glomerular disorder and renal tubular/interstitial disorder. Postrenal kidney disease is due to a problem in the urinary tract below the kidneys. Restoration of renal function can be expected if acute kidney injury is treated early, but if left without proper treatment it can progress to chronic kidney disease. According to the invention, therefore, D-alanine or its derivative may be administered for subjects suffering from or at risk of acute kidney injury.

Renal function can be assessed by measuring blood creatinine levels, total blood protein, blood urea nitrogen (BUN) and glomerular filtration rate. Creatinine levels, total blood protein, blood urea nitrogen (BUN) and estimated glomerular filtration rate are commonly measured in health examinations, and the D-alanine or its derivative of the invention may be administered to subjects having numerical values below standard levels or having a tendency toward deterioration.

Kidney disease is often accompanied by kidney inflammation, and renal function can be restored or kidney disease can be treated by inhibiting such disorder. Kidney disease includes glomerular nephritis and interstitial nephritis, where inflammation takes place in the glomerulus or interstitium. Glomerular nephritis is further classified as acute glomerular nephritis (acute nephritis) or chronic glomerular nephritis (chronic nephritis).

A prophylactic or ameliorative food for kidney disorder is a food indicated for ingestion by a subject suffering from kidney disorder or at risk of suffering from kidney disorder. Such foods include functional foods, health foods and supplements. D-Alanine or its derivative, or a material comprising it, can be added to any desired food. No adverse events have been reported when D-alanine is used as a food, even with ingestion on the order of 10 g, and any dosage may be set from the viewpoint of exhibiting a kidney-protecting effect or anti-inflammatory effect.

The term "treatment" is considered to be restoration of renal function or alleviation of kidney disorder. Although complete restoration of kidney disorder generally cannot be expected with chronic kidney disease, a composition for treatment according to the invention can be administered for the purpose of inhibiting deterioration. With acute kidney injury, a composition for treatment according to the invention may be administered for the purpose of restoring renal function. According to the invention, "prevention" is inhibiting onset or progression of, or restoration from, kidney disorder, for a subject suffering from or at risk of suffering from kidney disease.

The administered dosage of D-alanine may be selected as desired depending on the route of administration. The dosage may also be selected as desired based on animal testing or clinical trials. D-Alanine has no reported toxicity via oral administration, and the upper and lower limits for its dosage may be selected as desired from the viewpoint of exhibiting at least one function or effect from among a therapeutic effect or protective effect for kidney disease, a renal function restoration effect, an effect of suppressing inflammation of the kidneys and an effect of suppressing inflammatory cell death, by a protective effect on the kidneys, anti-inflammatory action and an inhibitory effect on inflammatory cell death.

The pharmaceutical composition of the invention may also include pharmacologically acceptable carriers, diluents or excipients in addition to the D-alanine or its derivative. The pharmaceutical composition of the invention may also comprise an anti-inflammatory drug or renal function-improving agent in addition to the D-alanine or its derivative. Such a pharmaceutical composition may be provided in a form suited for local administration (skin, inhalation, enema, eye drop, ear drop, nasal or intravaginal), enteral administration (oral, tubal or enteral) or parenteral administration (intravenous, transarterial, transdermal or intramuscular injection), with no limitation to these routes of administration.

The therapeutic agent or pharmaceutical composition of the invention may be formulated in a dosage form selected to be suitable for the route of administration. The dosage form may be designed as a tablet, capsule, liquid drug, powdered drug, granules or a chewable agent for use in oral administration, or as an injection, powdered drug or infusion preparation for parenteral administration. These formulations may also include various types of adjuvants such as carriers or other auxiliary agents that are used in drugs, including stabilizers, antiseptic agents, soothing agents, flavorings, taste correctives, aromatics, emulsifiers, fillers and pH adjustors, in ranges that do not interfere with the effect of the composition of the invention.

All of the publications mentioned throughout the present specification are incorporated herein in their entirety by reference. The examples of the invention described below are intended to serve merely as illustration and do not limit the technical scope of the invention. The technical scope of the invention is limited solely by the description in the Claims. Modifications of the invention, such as additions, deletions or substitutions to the constituent features of the invention, are possible so long as the gist of the invention is maintained.

EXAMPLES

Example 1: Inducing Kidney Disorder by Ischemia Reperfusion

1. Materials and Method (1) Research Ethics

All of the experiments were conducted according to facility guidelines, under the approval of the Animal Experiment Committee of the facility.

(2) Materials

Amino acid enantiomers and HPLC-grade acetonitrile were purchased from Nacalai Tesque, Inc. (Kyoto). HPLC-grade methanol, trifluoroacetic acid and boric acid were purchased from Wako Pure Chemical Industries, Ltd. (Osaka). The water was purified using a Milli-Q gradient A10 system.

(3) Animals

The animals were reared with free access to water and feed under conditions with an SPF environment and 12-hour light-dark cycling. C57BL/6J mice were purchased from Clea Japan, Inc. (Osaka).

(4) Renal Ischemia Reperfusion Treatment

Male 12- to 16-week-old mice were treated by renal ischemia reperfusion (hereunder also referred to as "I/R"). The renal pedicles were clamped with a non-traumatic clip (Natsume Seisakusho, Tokyo) under pentobarbital anesthesia to elicit ischemia. The clips were released after 40 minutes. The body temperature was kept at 37° C. during treatment.

The mice were reared with free access to water (control) or 20 mM D-alanine-containing water, prior to 14 days after IR treatment. On day 10 after IR treatment, the kidney tissues were sampled.

Staining

Figure 1:
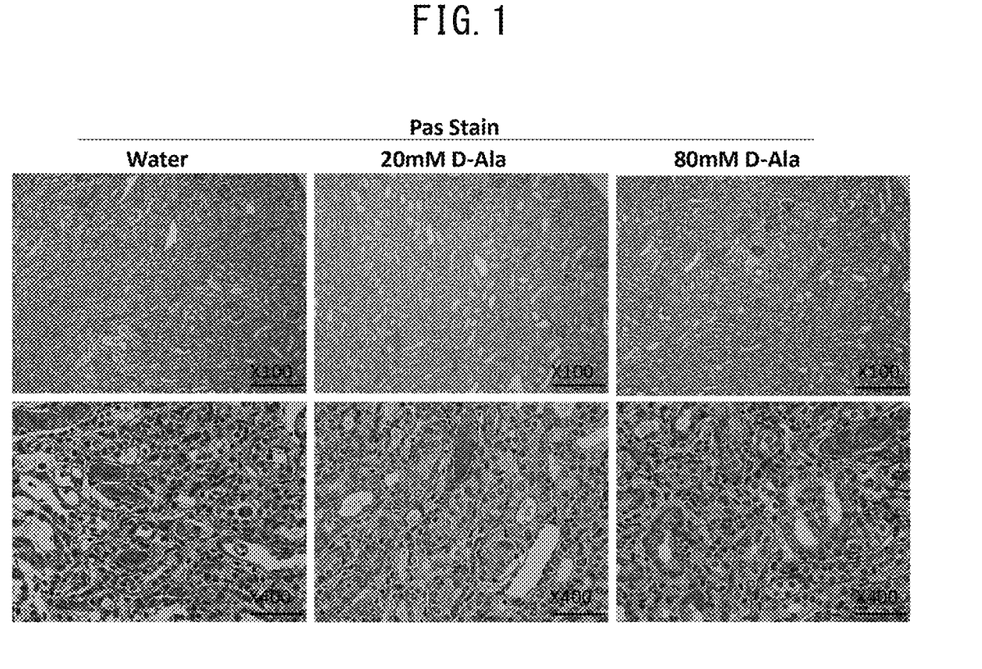
FIG. 1 shows a PAS-stained image of a kidney tissue section at 10 days after ischemia reperfusion (100× and 400× magnification). In the group given water, the staining intensity increased and accumulation of inflammatory cells such as neutrophils and eosinophils was observed, but in the group given D-alanine (20 mM and 80 mM), the staining intensity decreased in a dose-dependent manner.
Figure 2:
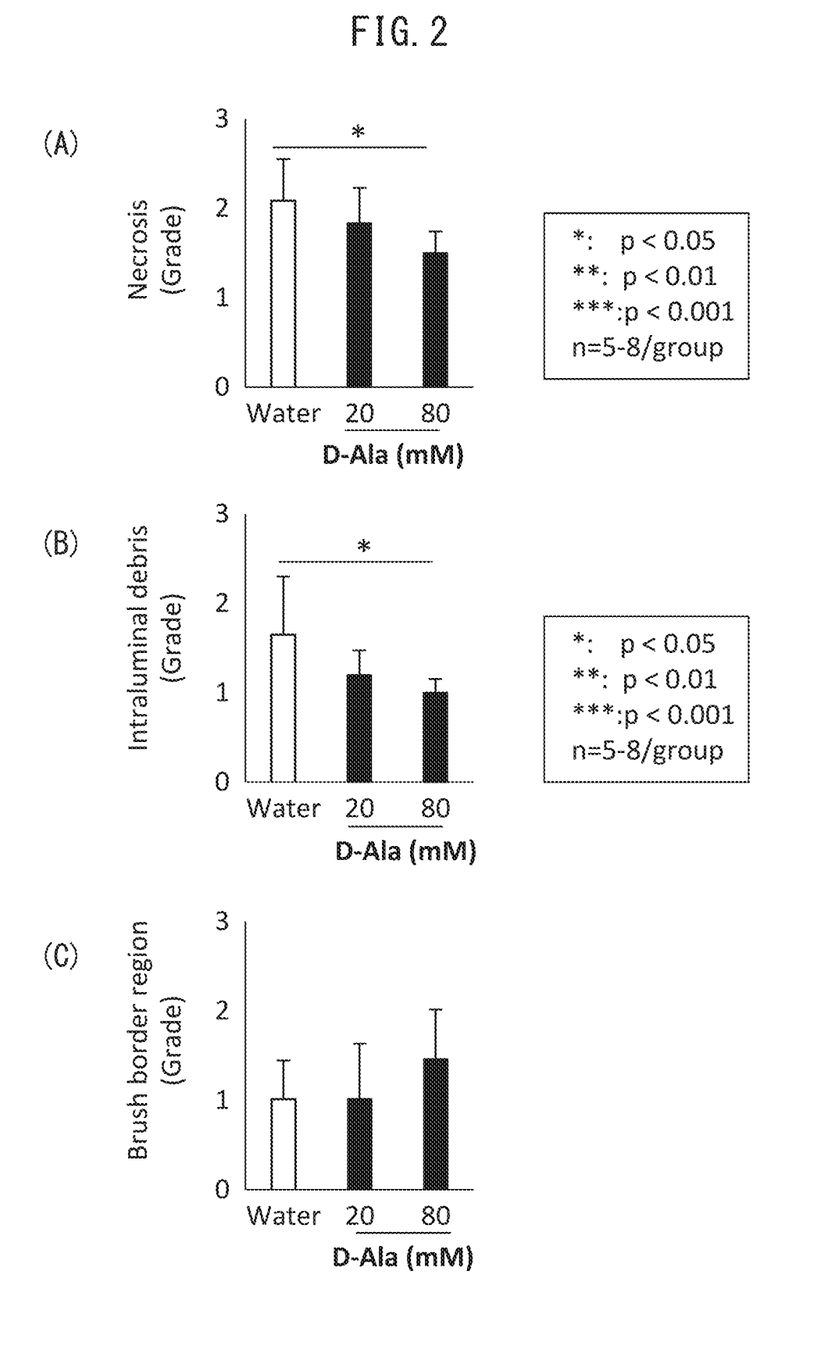
FIG. 2 shows grades of (A) necrosis, (B) intraluminal debris and (C) brush border region in a kidney tissue section at 10 days after ischemia reperfusion. The values improved in a dose-dependent manner in the group given D-alanine, compared with the group given water.

After ischemia reperfusion, the kidneys sampled on day 10 were fixed with 10% neutral buffered formalin and embedded in paraffin, and then stained with periodic acid-Schiff (PAS staining). The stained slices were photographed with a bright-field microscope (FIG. 1). Debris stained with PAS (skin boundary) or brush border (skin boundary and cortical region) were quantitatively evaluated in at least 10 different locations. The debris, renal tubular dilation, brush border damage, and renal tubule necrosis were evaluated by ATN score (0: none, 1: mild, 2: moderate, 3: severe). Sample evaluation was carried out blind. The results are shown in FIGS. 2(A) to (C).

Figure 3:
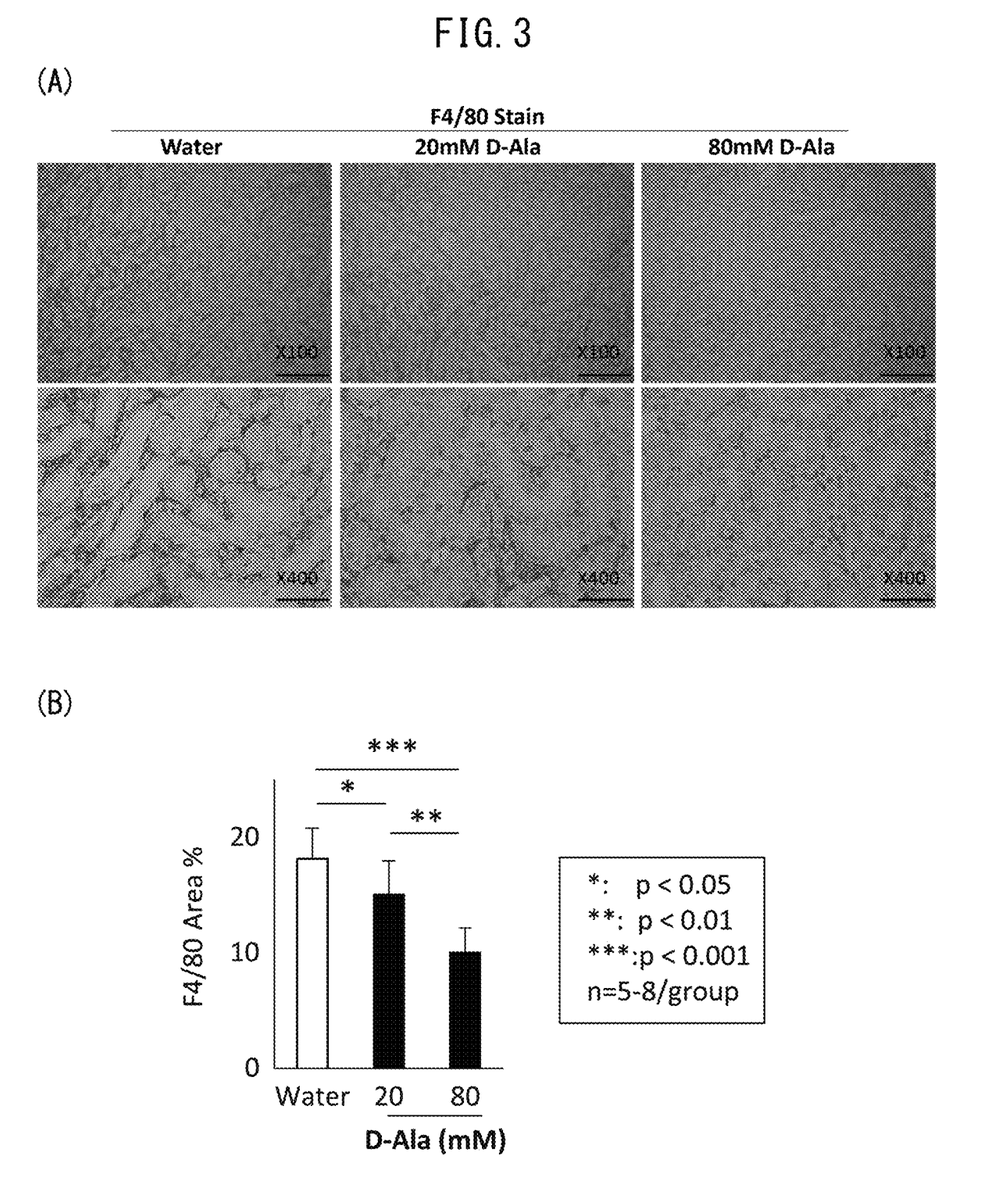
FIG. 3(A) shows an F4/80 stained image of a kidney tissue section at 10 days after ischemia reperfusion (100× and 400× magnification). In the group given water, the staining intensity increased and accumulation of inflammatory cells such as macrophages and monocytes was observed, but in the group given D-alanine, the staining intensity decreased in a dose-dependent manner.
FIG. 3(B) is a digitized diagram of the F4/80-stained region.

After ischemia reperfusion, the kidney tissues harvested on day 10 were fixed with 10% neutral buffered formalin and supplied for immunostaining using F4/80 antibody (Invitrogen, catalog #: MF48,000). F4/80 is a protein expressed specifically by macrophages, and it allows visualization of macrophages in kidney tissue. In the water-administered control group, cells stained with F4/80 were found accumulated in kidney tissue (day 5), but in the D-alanine-administered groups (20 mM and 80 mM) such cellular accumulation was minimal (FIG. 3(A)). The proportion of stained region in each group was measured (FIG. 3(B)).

Figure 4:
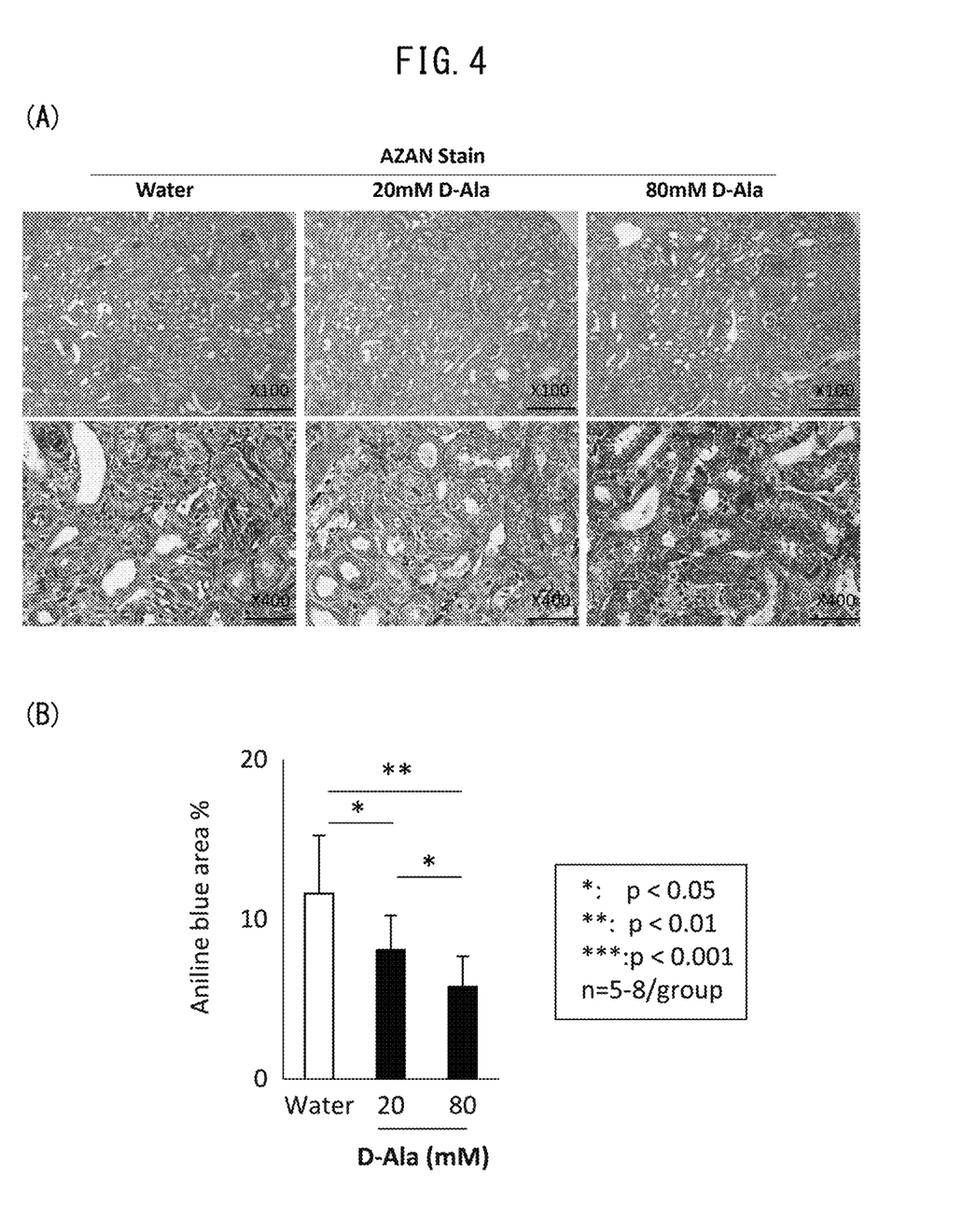
FIG. 4(A) shows an AZAN-stained image of a kidney tissue section at 10 days after ischemia reperfusion (100× and 400× magnification). In the group given water, the staining intensity increased and progressive fibrosis was observed, but in the group given D-alanine, the staining intensity decreased in a dose-dependent manner.
FIG. 4(B) is a digitized diagram of the AZAN-stained region.

After ischemia reperfusion, the kidney tissues sampled on day 10 were fixed with 10% neutral buffered formalin and provided for AZAN staining. In AZAN staining, fibrotic tissue is stained with aniline blue. In the water-administered control group, fibrotic tissue was seen over a wide area, but in the D-alanine-administered groups (20 mM and 80 mM), the aniline blue-stained regions were reduced in a dose-dependent manner (FIG. 4(A)). The proportion of stained region in each group was measured (FIG. 4(B)).

Example 2: Hypoxic Stress on Tubular Epithelial Cells (TEC)

Figure 5:
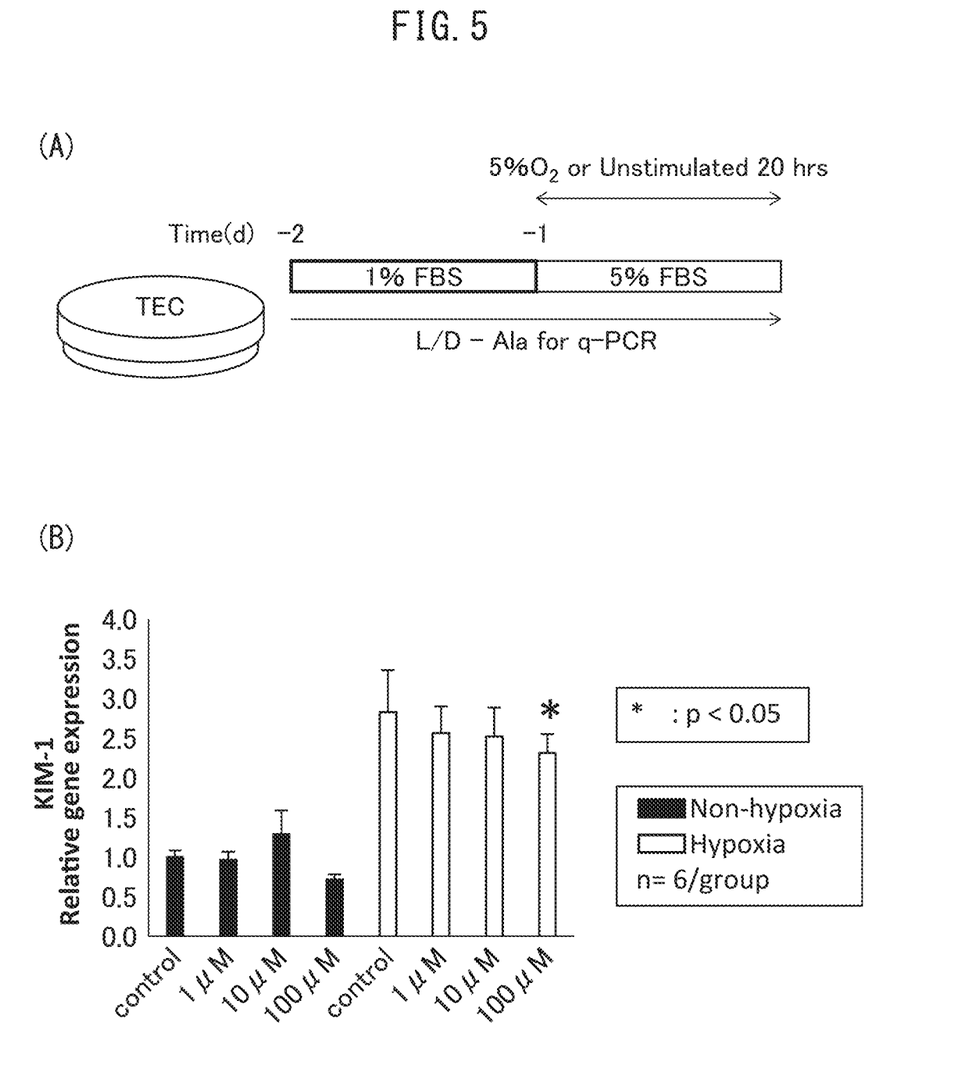
FIG. 5(A) shows a time schedule for addition of D-alanine to tubular epithelial cells (TEC), cultured under hypoxic stress conditions.
FIG. 5(B) shows changes in KIM-1 expression in response to D-alanine dose.

A mouse tubular epithelial cell line, mProx24cell, was provided from Sugaya (St. Marianna University School of Medicine, Tokyo). The cells were cultured in DMEM medium containing 5% fetal bovine serum (FBS) and 1% penicillin and streptomycin. The cultured cells were seeded using 1% FBS-added DMEM medium at $1.0 \times 10^6$ cell/well, and cultured for 24 hours in a 37° C., 5% $CO_2$ and 20% $O_2$ humidified atmosphere. In the hypoxic stress group, the 24 hours of culturing was followed by an additional 20 hours of culturing in 5% FBS-added DMEM medium in a 5% $CO_2$ and 5% $O_2$ humidified atmosphere, while in the non-hypoxic-stress group, it was followed by an additional 20 hours of culturing in a 5% FBS-added DMEM medium in a 5% $CO_2$ and 20% $O_2$ humidified atmosphere (FIG. 5(A)). D-Alanine was added as a test drug at 1 μM, 10 μM and 100 μM to each DMEM medium, but with no D-alanine added to the control.

Measurement of KIM-1 Gene Expression

The cultured cells were collected and the total RNA was extracted using a High Pure RNA Isolation Kit (Roche Diagnostics, Tokyo). Quantitative real-time PCR using SYBR Green fluorescence (Bio-Rad, Tokyo) was conducted with a Villa 7 Real-Time PCR System (Thermo Fisher Scientific, Tokyo), using the following primers. The data was analyzed by the delta-delta Ct method (FIG. 5(B)).

KIM-1 Forward: 5'-aggaagacccacggctattt-3' (SEQ ID NO: 1)

KIM-1 reverse: 5'-tgtcacagtgccattccagt-3' (SEQ ID NO: 2)

[Sequence Listing]

The invention claimed is:

1. A method for treatment of kidney disease, comprising: administrating D-alanine to a subject in need thereof, wherein the kidney disease is chronic kidney disease, ischemia-induced kidney disorder, or inflammation-induced kidney disorder.

2. The method according to claim 1, wherein the D-alanine is used for kidney protection or restoration of kidney function.

3. The method according to claim 1, wherein the administration is local administration, enteral administration or parenteral administration.

4. The method according to claim 1, wherein the kidney disease is chronic kidney disease.

5. The method according to claim 1, wherein the kidney disease is ischemia-induced kidney disorder.

6. The method according to claim 1, wherein the kidney disease is inflammation-induced kidney disorder.

* * * * *